(12) United States Patent
Higgins et al.

(10) Patent No.: US 8,834,703 B2
(45) Date of Patent: Sep. 16, 2014

(54) PREPARATION AND MAINTENANCE OF SENSORS

(75) Inventors: Michael Higgins, Huntington Beach, CA (US); Mark Konno, Laguna Beach, CA (US); Todd Fjield, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/430,492

(22) Filed: Mar. 26, 2012

(65) Prior Publication Data

US 2013/0075278 A1  Mar. 28, 2013

Related U.S. Application Data

(63) Continuation of application No. 12/276,230, filed on Nov. 21, 2008, now abandoned.

(60) Provisional application No. 60/990,797, filed on Nov. 28, 2007.

(51) Int. Cl.
| | |
|---|---|
| *G01F 1/64* | (2006.01) |
| *C12Q 1/00* | (2006.01) |
| *G01N 27/26* | (2006.01) |
| *G01N 33/50* | (2006.01) |
| *G01N 33/487* | (2006.01) |
| *G01N 27/327* | (2006.01) |
| *A61B 5/1486* | (2006.01) |
| *A61B 5/145* | (2006.01) |
| *A61B 5/1495* | (2006.01) |

(52) U.S. Cl.
CPC .......... *G01N 27/327* (2013.01); *G01N 33/4875* (2013.01); *A61B 2562/242* (2013.01); *A61B 5/1495* (2013.01); *A61B 5/1486* (2013.01); *A61B 5/14532* (2013.01)
USPC ... 205/777.5; 205/792; 205/775; 204/403.01; 204/403.04

(58) Field of Classification Search
CPC .................................. G01N 27/3271–27/3278
USPC ......... 204/403.01–403.15; 205/775, 792, 777
See application file for complete search history.

(56) References Cited

U.S. PATENT DOCUMENTS

| | | |
|---|---|---|
| 4,223,110 A | 9/1980 | Phillips et al. |
| 4,271,278 A | 6/1981 | Phillips et al. |

(Continued)

FOREIGN PATENT DOCUMENTS

| | | |
|---|---|---|
| DE | 4405149 A1 | 9/1994 |
| DE | 102004056587 A1 | 5/2006 |

(Continued)

OTHER PUBLICATIONS

International Search Report, Mar. 19, 2009.

(Continued)

*Primary Examiner* — Luan Van
*Assistant Examiner* — Maris R Kessel
(74) *Attorney, Agent, or Firm* — Michael Crapenhoft

(57) ABSTRACT

Apparatus and methods are described for preparing, maintaining, and stabilizing sensors. The apparatus and methods for preparing sensors for use are utilized in advance of the sensor being removed from a sealed, sterilized package. The apparatus include packaging materials having electrical circuits capable of stabilizing a sensor to prepare the sensor for use. The methods for preparing a sensor for use includes methods of providing a solution to a sterilized packaging that contains a sensor connected to a sensor activating circuit, activating the circuit, and allowing the sensor to stabilize. These methods can be performed without compromising the packaging. The apparatus for stabilizing a sensor that is in use include a circuit connectable to the sensor that provides a signal to the sensor that prevents the sensor from becoming destabilized when disconnected from a monitoring device.

7 Claims, 5 Drawing Sheets

(56) References Cited

U.S. PATENT DOCUMENTS

| | | | |
|---|---|---|---|
| 4,352,360 A | 10/1982 | King | |
| 4,398,346 A | 8/1983 | Underhill et al. | |
| 4,430,397 A | 2/1984 | Untereker | |
| 4,465,743 A | 8/1984 | Skarstad et al. | |
| 4,542,291 A | 9/1985 | Zimmerman | |
| 4,549,952 A | 10/1985 | Columbus | |
| 4,608,322 A | 8/1986 | Howard et al. | |
| 4,703,756 A * | 11/1987 | Gough et al. | 600/347 |
| 4,863,016 A | 9/1989 | Fong et al. | |
| 4,937,444 A | 6/1990 | Zimmerman | |
| 4,983,524 A | 1/1991 | Fujikawa et al. | |
| 5,165,407 A | 11/1992 | Wilson et al. | |
| 5,178,267 A | 1/1993 | Grabenkort et al. | |
| 5,229,282 A | 7/1993 | Yoshioka et al. | |
| 5,278,200 A | 1/1994 | Coury et al. | |
| 5,328,848 A | 7/1994 | Fong et al. | |
| 5,331,966 A | 7/1994 | Bennett et al. | |
| 5,352,348 A | 10/1994 | Young et al. | |
| 5,390,671 A | 2/1995 | Lord et al. | |
| 5,391,250 A | 2/1995 | Cheney, II et al. | |
| 5,421,981 A * | 6/1995 | Leader et al. | 204/403.13 |
| 5,423,883 A | 6/1995 | Helland | |
| 5,429,735 A | 7/1995 | Johnson et al. | |
| 5,434,017 A | 7/1995 | Berkowitz et al. | |
| 5,439,760 A | 8/1995 | Howard et al. | |
| 5,455,123 A | 10/1995 | Helgeson et al. | |
| 5,455,999 A | 10/1995 | Weiss et al. | |
| 5,458,997 A | 10/1995 | Crespi et al. | |
| 5,482,473 A | 1/1996 | Lord et al. | |
| 5,486,215 A | 1/1996 | Kelm et al. | |
| 5,538,511 A | 7/1996 | Van Antwerp | |
| 5,549,985 A | 8/1996 | Heller et al. | |
| 5,568,806 A | 10/1996 | Cheney, II et al. | |
| 5,569,186 A | 10/1996 | Lord et al. | |
| 5,586,553 A | 12/1996 | Halili et al. | |
| 5,607,463 A | 3/1997 | Schwartz et al. | |
| 5,607,565 A | 3/1997 | Azarnia et al. | |
| 5,665,065 A | 9/1997 | Colman et al. | |
| 5,728,420 A | 3/1998 | Keogh | |
| 5,741,211 A | 4/1998 | Renirie et al. | |
| 5,766,839 A | 6/1998 | Johnson et al. | |
| 5,777,060 A | 7/1998 | Van Antwerp | |
| 5,779,665 A | 7/1998 | Mastrototaro et al. | |
| 5,786,439 A | 7/1998 | Van Antwerp et al. | |
| 5,788,678 A | 8/1998 | Van Antwerp | |
| 5,838,546 A | 11/1998 | Miyoshi | |
| 5,891,506 A | 4/1999 | Keogh | |
| 5,914,179 A | 6/1999 | Inaba | |
| 5,919,216 A | 7/1999 | Houben et al. | |
| 5,925,552 A | 7/1999 | Keogh et al. | |
| 5,945,319 A | 8/1999 | Keogh | |
| 5,951,521 A | 9/1999 | Mastrototaro et al. | |
| 5,965,380 A | 10/1999 | Heller et al. | |
| 5,987,361 A | 11/1999 | Mortimer | |
| 5,992,211 A | 11/1999 | Skrtic | |
| 5,994,444 A | 11/1999 | Trescony et al. | |
| 6,017,741 A | 1/2000 | Keogh | |
| 6,033,719 A | 3/2000 | Keogh | |
| 6,038,475 A | 3/2000 | Sikorski et al. | |
| 6,071,391 A | 6/2000 | Gotoh et al. | |
| 6,093,167 A | 7/2000 | Houben et al. | |
| 6,093,172 A | 7/2000 | Funderburk et al. | |
| 6,093,506 A | 7/2000 | Crespi et al. | |
| 6,101,973 A | 8/2000 | Stewart et al. | |
| 6,118,652 A | 9/2000 | Casby et al. | |
| 6,125,291 A | 9/2000 | Miesel et al. | |
| 6,129,742 A | 10/2000 | Wu et al. | |
| 6,134,459 A | 10/2000 | Roberts et al. | |
| 6,134,461 A | 10/2000 | Say et al. | |
| 6,135,978 A | 10/2000 | Houben et al. | |
| D433,755 S | 11/2000 | Mastrototaro et al. | |
| 6,143,354 A | 11/2000 | Koulik et al. | |
| 6,144,866 A | 11/2000 | Miesel et al. | |
| 6,163,723 A | 12/2000 | Roberts et al. | |
| 6,175,752 B1 | 1/2001 | Say et al. | |
| 6,176,988 B1 | 1/2001 | Kessler | |
| 6,198,952 B1 | 3/2001 | Miesel | |
| 6,200,265 B1 | 3/2001 | Walsh et al. | |
| 6,205,358 B1 | 3/2001 | Haeg et al. | |
| 6,212,416 B1 | 4/2001 | Ward et al. | |
| 6,218,016 B1 | 4/2001 | Tedeschi et al. | |
| 6,223,083 B1 | 4/2001 | Rosar | |
| 6,248,067 B1 | 6/2001 | Causey, III et al. | |
| 6,252,032 B1 | 6/2001 | Van Antwerp et al. | |
| 6,254,586 B1 | 7/2001 | Mann et al. | |
| 6,261,280 B1 | 7/2001 | Houben et al. | |
| 6,274,265 B1 | 8/2001 | Kraska et al. | |
| 6,284,478 B1 | 9/2001 | Heller et al. | |
| 6,292,697 B1 | 9/2001 | Roberts | |
| 6,293,925 B1 | 9/2001 | Safabash et al. | |
| 6,295,473 B1 | 9/2001 | Rosar | |
| 6,303,179 B1 | 10/2001 | Koulik et al. | |
| D452,323 S | 12/2001 | Mastrototaro et al. | |
| 6,329,161 B1 | 12/2001 | Heller et al. | |
| 6,340,421 B1 | 1/2002 | Vachon et al. | |
| 6,360,888 B1 | 3/2002 | McIvor et al. | |
| 6,368,274 B1 | 4/2002 | Van Antwerp et al. | |
| 6,413,393 B1 | 7/2002 | Van Antwerp et al. | |
| 6,418,332 B1 | 7/2002 | Mastrototaro et al. | |
| 6,424,847 B1 | 7/2002 | Mastrototaro et al. | |
| 6,438,407 B1 | 8/2002 | Ousdigian et al. | |
| 6,456,875 B1 | 9/2002 | Wilkinson et al. | |
| 6,462,162 B2 | 10/2002 | Van Antwerp et al. | |
| 6,477,395 B2 | 11/2002 | Schulman et al. | |
| 6,484,045 B1 | 11/2002 | Holker et al. | |
| 6,484,046 B1 | 11/2002 | Say et al. | |
| D469,540 S | 1/2003 | Holker et al. | |
| 6,512,939 B1 | 1/2003 | Colvin et al. | |
| 6,520,326 B2 | 2/2003 | McIvor et al. | |
| 6,558,345 B1 | 5/2003 | Houben et al. | |
| 6,558,351 B1 | 5/2003 | Steil et al. | |
| 6,558,734 B2 | 5/2003 | Koulik et al. | |
| 6,560,471 B1 | 5/2003 | Heller et al. | |
| 6,565,509 B1 | 5/2003 | Say et al. | |
| 6,572,542 B1 | 6/2003 | Houben et al. | |
| 6,572,748 B1 | 6/2003 | Herrmann et al. | |
| 6,577,899 B2 | 6/2003 | Lebel et al. | |
| 6,592,746 B1 | 7/2003 | Schmid-Schoenbein et al. | |
| 6,605,039 B2 | 8/2003 | Houben et al. | |
| 6,617,142 B2 | 9/2003 | Keogh et al. | |
| 6,641,533 B2 | 11/2003 | Causey, III et al. | |
| 6,642,015 B2 | 11/2003 | Vachon et al. | |
| 6,666,821 B2 | 12/2003 | Keimel | |
| 6,669,663 B1 | 12/2003 | Thompson | |
| 6,671,554 B2 | 12/2003 | Gibson et al. | |
| 6,731,976 B2 | 5/2004 | Penn et al. | |
| 6,895,263 B2 | 5/2005 | Shin et al. | |
| 6,895,265 B2 | 5/2005 | Silver | |
| 6,899,813 B2 | 5/2005 | Dolecek et al. | |
| 6,908,535 B2 | 6/2005 | Rankin et al. | |
| 6,915,147 B2 | 7/2005 | Lebel et al. | |
| 6,922,330 B2 | 7/2005 | Nielsen et al. | |
| 6,923,936 B2 | 8/2005 | Swanson et al. | |
| 6,940,141 B2 | 9/2005 | Kinsman | |
| 6,942,518 B2 | 9/2005 | Liamos et al. | |
| 6,960,466 B2 | 11/2005 | Pamidi et al. | |
| 6,972,423 B2 | 12/2005 | Welland et al. | |
| 6,973,706 B2 | 12/2005 | Say et al. | |
| 6,985,764 B2 | 1/2006 | Mason et al. | |
| 6,991,096 B2 * | 1/2006 | Gottlieb et al. | 206/210 |
| 7,003,336 B2 | 2/2006 | Holker et al. | |
| 7,003,340 B2 | 2/2006 | Say et al. | |
| 7,003,341 B2 | 2/2006 | Say et al. | |
| 7,006,858 B2 | 2/2006 | Silver et al. | |
| 7,018,336 B2 | 3/2006 | Enegren et al. | |
| 7,022,072 B2 | 4/2006 | Fox et al. | |
| 7,029,444 B2 | 4/2006 | Shin et al. | |
| 7,122,390 B2 | 10/2006 | Kinsman | |
| 7,241,266 B2 | 7/2007 | Zhou et al. | |
| 7,279,174 B2 | 10/2007 | Pacetti et al. | |
| 7,297,112 B2 | 11/2007 | Zhou et al. | |
| 2002/0072084 A1 | 6/2002 | Meserol et al. | |
| 2003/0153900 A1 | 8/2003 | Aceti et al. | |
| 2004/0058453 A1 | 3/2004 | Free et al. | |

(56) References Cited

U.S. PATENT DOCUMENTS

| | | | |
|---|---|---|---|
| 2004/0137633 | A1 | 7/2004 | Shin et al. |
| 2004/0191428 | A1 | 9/2004 | Tsuda et al. |
| 2004/0208785 | A1 | 10/2004 | Seto et al. |
| 2004/0222091 | A1* | 11/2004 | Lauks et al. ............... 204/400 |
| 2005/0233407 | A1 | 10/2005 | Pamidi et al. |
| 2005/0261562 | A1 | 11/2005 | Zhou et al. |
| 2006/0282001 | A1 | 12/2006 | Noel et al. |
| 2007/0200254 | A1 | 8/2007 | Curry |
| 2007/0202562 | A1 | 8/2007 | Curry |
| 2007/0202672 | A1 | 8/2007 | Curry |
| 2007/0219441 | A1 | 9/2007 | Carlin et al. |
| 2007/0249007 | A1 | 10/2007 | Rosero |
| 2008/0029390 | A1 | 2/2008 | Roche et al. |
| 2008/0033264 | A1 | 2/2008 | Lonneker-Lammers et al. |
| 2008/0033273 | A1 | 2/2008 | Zhou et al. |
| 2008/0125751 | A1 | 5/2008 | Fjield et al. |
| 2008/0200788 | A1 | 8/2008 | Brister et al. |
| 2008/0307854 | A1 | 12/2008 | Kraus |

FOREIGN PATENT DOCUMENTS

| | | |
|---|---|---|
| DE | 202006016617 U1 | 1/2007 |
| EP | 0351851 A2 | 1/1990 |
| JP | 63300953 A | 12/1988 |
| WO | WO-96/11626 A1 | 4/1996 |
| WO | WO-02/102224 A2 | 12/2002 |
| WO | WO-03/035117 A1 | 5/2003 |
| WO | WO-2005/074612 A2 | 8/2005 |
| WO | WO-2006/005033 A2 | 1/2006 |
| WO | WO-2006/040106 A1 | 4/2006 |
| WO | WO-2007/098187 A2 | 8/2007 |
| WO | WO-2007100588 A1 | 9/2007 |
| WO | WO-2008/141243 A2 | 11/2008 |

OTHER PUBLICATIONS

Lisette B. Verbrugge MD, Deborah Crisis, RN, M Higgins BSce, MBA and Harry B van Wezel MD, PhD, "Accuracy of a Prototype Central Venous Continuous Amperometric Glucose Sensor," American Society of Anesthesiology (ASA) meeting in Oct. 2007.

Fiorito et al.; Glucose Amperometric Biosensor Based on the Co-immobilizationi of Glucose Oxidase (GOx) and Ferrocene in Poly(pyrrole) Generated from ethauol/ water mixtures; J. Braz. Chem. Soc., vol. 12. No. 6 729-733,2001.

Garg et al., "Improvement in Glycemic Excursions with a Transcutaneous, Real-Time Continuous Glucose Sensor,"Diabetes Care, (2006) 29: 44-50.

Krajewska; "Application of chitin- and chitosan based materials for enzyme immobilization: a review;" Enzyme Microb Technol 35 (2004), pp. 126-139.

Markey et al., "Immobilization of Catalase and Glucose Oxidase on Inorganic Supports," Biotechnology and Engineering (1975) 17:285.

Miao, et al. ; "Amperometric Glucose Biosensor Based on Immobilization of Glucose Oxidase in Chitosan Matrix cross-linked with glutaraldehyde," Electroanalysis (2001) 46:347-49.

Renard, "Implantable Glucose Sensors for Diabetes Monitoring,"Minim Invasive Ther Allied Technol, 13:78-86 (2004).

Sternberg, et al., "Study and Development of Multilayer Needle-type Enzyme-based Glucose Microsensors," Biosensors 4: 27-40 (1988).

Urban, et al.; "Minitaurized thin-film biosensors using covalently immobilized glucose oxidase," May 4, 1990; accepted Jan. 23, 1991; Biosensors & Bioelectronics 6 (1991) 555-562.

Updike et al., "The Enzyme Electrode," Nature. vol. 214: 986 (1967).

Wang, "Glucose Biosensors: 40 Years of Advances and Challenges, "Electroanalysis, vol. 13, No. 12, pp. 983-988 (2001).

European Patent Office Action, Oct. 15, 2012.

\* cited by examiner

PREPARATION AND MAINTENANCE OF SENSORS

CROSS-REFERENCE TO RELATED APPLICATION

This application is a continuation of U.S. patent application Ser. No. 12/276,230 filed Nov. 21, 2008 and claims priority from U.S. provisional patent application No. 60/990,797, filed on Nov. 28, 2007, which is also hereby incorporated herein by reference.

BACKGROUND

Before some sensors are capable of making their intended measurements, they go through some form of conditioning. The time it takes a sensor to be conditioned and become capable of making measurements is often referred to as its run-in period. Run-in periods can last for as little as a few minutes to as long as a few days. The type of conditioning and run-in time required for each type or kind of sensor will vary depending on the condition of the sensor and the intended purpose and design of the sensor being used. For example, electrochemical sensors often contain electrodes at which electrochemical reactions take place, an electrolytic solution or transport matrix in which the reactions take place, and a membrane to control the access of analyte species. Examples of the types of conditions that control the length of run-in time include the time it takes for the appropriate oxidation or reduction of chemical species at the electrodes before the desired reactions to take place, the consistency of the electrolytic solution or transport matrix, and the hydration of the membrane. Regardless of the type of conditioning required for a particular sensor, a sensor sealed within a container without access to required compounds or signals cannot undergo run-in conditioning.

SUMMARY

Apparatus and methods for preparing and maintaining sensors, such as electrochemical sensors, are disclosed. The apparatus and methods for preparing sensors are utilized in advance of the sensor being removed from a sealed sterilized package. The apparatus for preparing sensors include packaging materials incorporating electrical circuits capable of exciting or stabilizing a sensor. The methods for preparing sensors include methods of providing a solution to a sterilized packaging containing a sensor connected to a sensor activating circuit without compromising the sterilizable packaging, activating a circuit electrically connected to the sensor, and allowing the sensor to stabilize. The providing and activating steps preferably occur without breaching the sterilized packaging.

Further disclosed are apparatus for stabilizing a sensor that is in use. These apparatus include a circuit connectable to the sensor that provides a signal to the sensor that prevents the sensor from becoming destabilized when disconnected from a monitoring device. Such a circuit can prevent a sensor from becoming depolarized by, for example, providing an appropriate electrical current or potential. These apparatus can also include a rechargeable voltage source and/or a recordable storage medium that is capable of recording data related to a sensor.

DESCRIPTION OF DRAWINGS

Like reference numerals and symbols in the various drawings indicate like elements.

DETAILED DESCRIPTION

Apparatus and methods for preparing and maintaining sensors for use are disclosed herein. The apparatus and methods for preparing sensors for use are utilized in advance of the sensor being removed from a sealed sterilized package. The apparatus include packaging materials having electrical circuits capable of stabilizing a sensor to prepare the sensor for use. The methods for preparing a sensor for use include methods of providing a solution to a sterilized packaging that contains a sensor and activating a circuit electrically connected to the sensor. These methods can be performed without compromising the sterilized packaging and allow time for the sensor to stabilize.

Further disclosed herein are apparatus for stabilizing a sensor that is in use. These apparatus include a circuit connectable to the sensor that provides a signal to the sensor that prevents the sensor from becoming destabilized when disconnected from a monitoring device. A circuit for stabilizing a sensor during use can be similar to or the same as a circuit for preparing a sensor for use.

Figure 1:
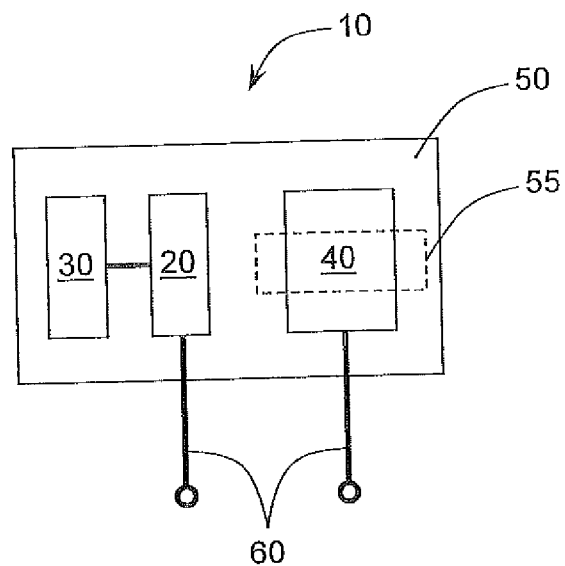
FIG. 1 is an illustration of an electrochemical sensor.

As shown in FIG. 1, a sensor 10 for measuring an analyte includes a reference electrode 20, an optional counter electrode 30, and a working electrode 40 provided on a substrate 50. The electrodes (20, 30, 40) are formed of a conductive material. The reference electrode 20 can be, for example, an Ag/AgCl electrode. The counter electrode 30 and working electrode 40 can be, for example, graphite and platinum. In operation, the reference electrode 20 establishes a fixed potential from which the potential of the counter electrode 30 and working electrode 40 can be established. The counter electrode 30 provides a working area for conducting the majority of electrons from, for example, an oxidation reaction back to the solution being analyzed, i.e., blood. Otherwise the current generated from the chemical reaction would pass through the reference electrode 20 and possibly reduce its service life. Electrically conductive wires 60 are connected to the reference electrode 20 and working electrode 40 for applying and/or measuring current or potential at or between the electrodes. Although the sensor 10 shown in FIG. 1 includes one reference electrode 20, one counter electrode 30, and one working electrode 40, electrochemical sensors can include multiple reference electrodes, counter electrodes, and working electrodes as would be understood by one of skill in the art.

Figure 1A:
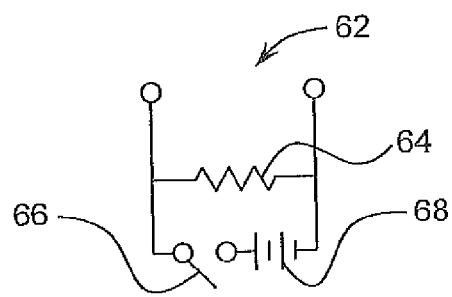
FIG. 1A is a schematic of a circuit.

The electrically conductive wires 60 can be connected to a circuit. An example of a circuit 62 is shown in FIG. 1A. A circuit 62 can include a parallel resistor 64 to limit voltage drop, a switch 66, and a voltage source 68 such as a battery, as shown in FIG. 1A. Such a circuit 62 can be a current controlled voltage source that provides a constant voltage. An example of a range of voltages for use in such a circuit 62 is about 0.2 V to about 2 V, other ranges of voltages include about 0.4 V to about 1.5 V, about 0.5 V to about 1 V, and about 0.6 V to about 0.7 V. Other circuit designs that provide a current controlled voltage source that provides a constant voltage will be apparent to one of skill in the art. For example, other electrical components can be used instead of or with the parallel resistor 64 such as a capacitor to help control the voltage of the circuit.

Figure 2:
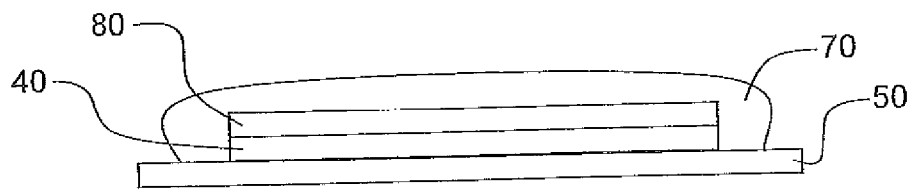
FIG. 2 is a cross-sectional view of the working electrode of the electrochemical sensor of FIG. 1.

FIG. 2 shows a cross-section of the area enclosed by the dashed area 55 in FIG. 1. In FIG. 2, the working electrode 40 is covered by an analyte selective membrane 70 which also covers a reagent layer 80. Reagent layer 80 is selected to react with one or more specific analytes found or expected to be found in a fluid to be analyzed. For example, in a glucose biosensor, the reagent layer 80 can contain glucose oxidase, such as may be derived from *Aspergillus niger* (EC 1.1.3.4), type II or type VII. Reagent layer 80 can also include a matrix such as a hydrogel to promote a reaction between the reagent and an analyte that passes through the membrane 70. A hydrogel, for example, can be water absorbent and swell to provide active transport of an analyte in a fluid under analysis (e.g., glucose) from the fluid into the reagent layer 80.

Figure 3:
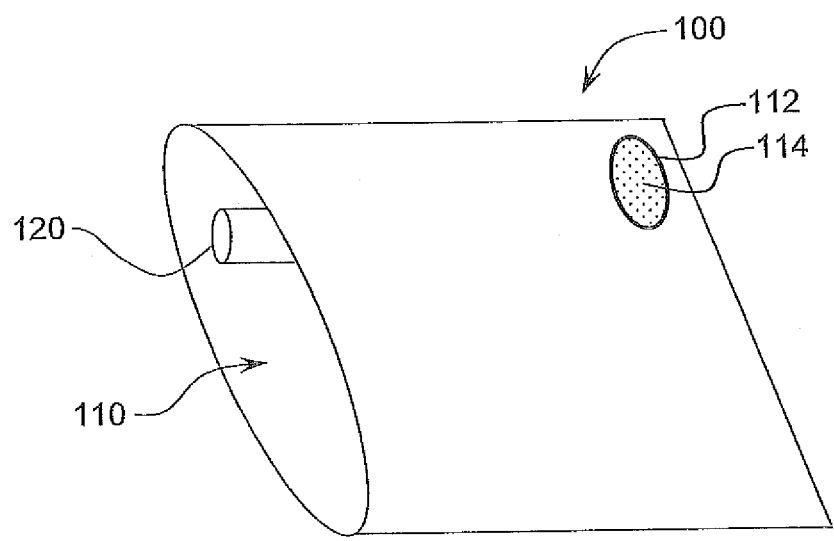
FIG. 3 is a perspective view of a sterilizable packaging in the form of a sealable pouch.

An apparatus for preparing a sensor for use in advance of the sensor being removed from a sealed sterilized package is shown in FIG. 3. FIG. 3 is a perspective view of a sterilizable packaging in the form of a sealable pouch 100. Although FIG. 3 illustrates a sealable pouch 100, any other form of sterilizable packaging can be used in accordance with the invention. The sealable pouch 100 is made of a material such as a polymer that can maintain a sterilized environment and is typically liquid and vapor impermeable. The sealable pouch 100 is referred to as being sealable rather than sealed because, as depicted, one end 110 is open. The sealable pouch 100 can be sealed using an adhesive composition or heat sealing (melting) in the case of a polymer. Techniques for sealing sterilized containers are well known to those of skill in the art. The sealable pouch 100 can be made from flexible materials or a mixture of flexible, rigid, or substantially rigid materials. For example, the sealable pouch could include a rigid back portion, i.e., a rigid backing, and a flexible front portion.

Figure 4:
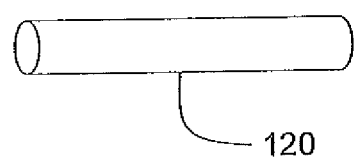
FIG. 4 is a rupturable solution container in the shape of a cylinder.

Also shown in FIG. 3 is a resealable portion 112. The resealable portion 112 can be used to provide solution to the sealable pouch 100. The resealable portion 112 can for example be a self-sealing membrane 114 through which a syringe can be inserted. Alternatively, or in addition to the resealable portion 112 is shown a partial view of a rupturable solution container 120 that is inserted into the sealable pouch 100. The rupturable solution container 120 is also shown in FIG. 4. As shown, the rupturable solution container 120 is cylindrical, though other shapes and configurations are possible. Additionally, the size of the rupturable solution container 120 can be varied to accommodate the volume of solution desired to be delivered to the sealable pouch 100.

The rupturable solution container 120 is made from a material, such as a polymer, that is more easily ruptured than the material used to make the sealable pouch 100. A more easily ruptured material is used so the rupturable solution container 120 can be ruptured while on the interior of the sealable pouch 100 using forces that will not breach the sealable pouch 100. For example, the sealable pouch 100 will not be breached at any point along the material used to form the sealable pouch 100 or any point where two or more portions of the sealable pouch 100 are sealed together, e.g., along a seam, when the rupturable container is ruptured. The ability to maintain the integrity of the sealable pouch 100 allows the maintenance of a sterilized state for any contents of the sealable pouch 100. The rupturable solution container 120 can be attached to an inner portion of the sealable pouch 100 through the use, for example, of an adhesive or by forming the rupturable solution container as part of the sealable pouch. Attaching the rupturable solution container 120 to an inner portion of the sealable pouch 100 can provide consistency in the positioning of the rupturable solution container 120 for ease of use. The terms rupture and breach and their derivatives are used herein to indicate that a container has been opened such that the contents of a container are able to move from the interior of the container to the exterior of the container. It is noted that the solution can be provided in the rupturable solution container 120 when the sealable pouch 100 is sealed and shipped and/or stored, or the sealable pouch can be sealed and the rupturable solution container filled through the use of a resealable portion 112 and a syringe as discussed above.

Figure 5:
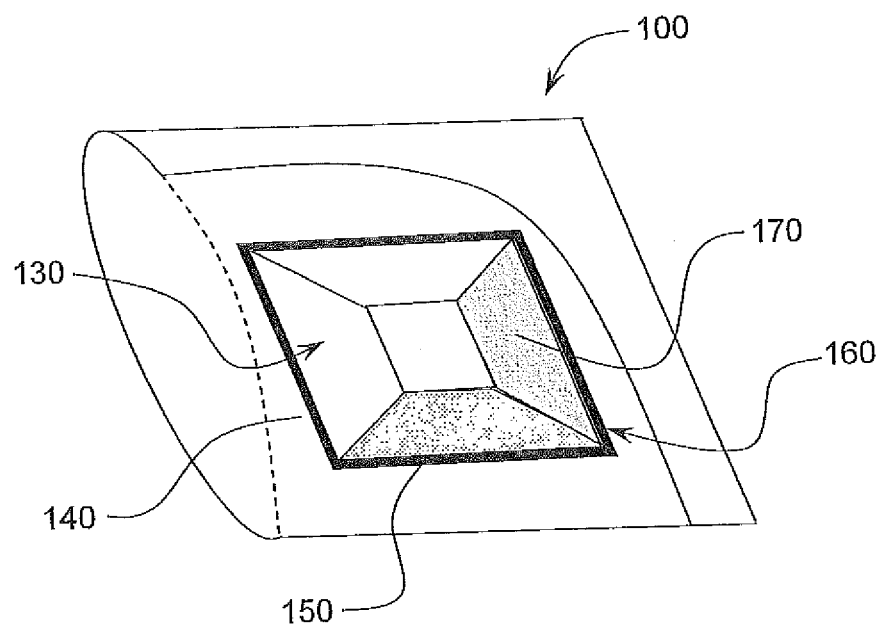
FIG. 5 is a cut away view of a sealable pouch with an alternative embodiment of a rupturable solution container that is partially formed using the back portion of the sealable pouch.

An alternative design for the rupturable solution container 130 is shown in FIG. 5. In FIG. 5, a rupturable solution container 130 is shown in which a portion of the rupturable solution container 130 is formed by an interior surface 140 of the sealable pouch 100. A seal 150 between the perimeter 160 of the rupturable solution container 130 and the interior surface 140 of the sealable pouch 100 attaches the rupturable solution container 130 to the interior surface 140 of the sealable pouch 100 and prevents solution from leaking prematurely from the rupturable solution container 130. In this embodiment of a rupturable solution container 130, the more easily ruptured material is used to form the interior side 170 of the rupturable solution container 130, which ruptures prior to a breach of the material used to form the sealable pouch 100 to allow the solution into the sealable pouch 100.

The types of polymers or other materials for use in such containers can include, for example, polypropylene or polyethylene film or sheet. The tear strength, i.e., the resistance of a material to tear forces (as might be measured by ASTM D 1922), is a relevant property for the apparatus and methods described herein. For example, the relative tear strengths of the materials used for the rupturable solution container 120 and the sealable pouch 100 are important in determining the material for use as the rupturable solution container 120 in that the tear strength of the material for use as the rupturable solution container 120 will be less than the tear strength of the sealable pouch 100.

The sealable pouch 100 described herein can be used to contain a sensor such as an electrochemical sensor. An example of an electrochemical sensor is a blood glucose sensor. The run-in period for a sensor located in a sealable pouch 100 as described herein that has a sensor sealed inside can be begun by providing an electrolytic, i.e., conductive, solution to the sealable pouch 100. The electrolytic solution can be medically safe and non-toxic, e.g., sterile saline. The electrolytic solution can be provided from an external source or contained, for example, in a rupturable solution container 120, which can provide solution to the sealable pouch 100 when ruptured. As used herein, run-in time is the time it takes for the sensor to reach equilibrium and to be ready for measurement. Once the electrolytic solution is provided or the rupturable solution container 120 is breached, the solution can spread into the sealable pouch 100 and contact the sensor. Electrolytic solution can be provided, for example, by introducing a solution through a resealable portion of the sealable pouch, such as, for example, by injection through the resealable membrane 114.

Once contacted by the solution, the run-in period can begin with respect to, for example, hydration. Run-in time can be considered to include multiple phases such as hydration (i.e., the time for the sensor to come into contact and equilibrate with a solution) and polarization (i.e., the time for the sensor to stabilize once voltage is applied to the sensor). These phases can occur simultaneously or overlap. If aspects of the sensor other than hydration remain to be activated or run-in after exposure to the solution, such as aspects of the sensor that are dependent on the presence of an electric potential, these aspects for preparing the electrode can then be performed after the solution is added. If the circuit is connected to the sensor prior to the addition of solution, both hydration and electrical stabilization can begin as soon as the system comes into contact with the electrolytic solution. Electrical stabilization of the sensor can include non-Faradaic responses.

Figure 6:
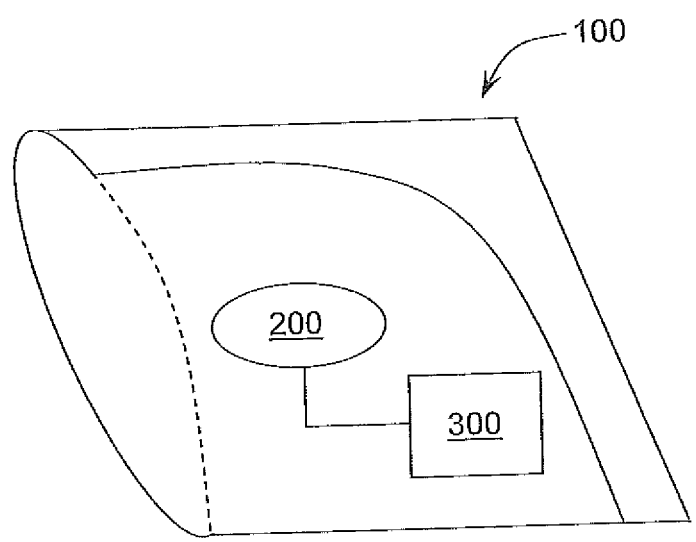
FIG. 6 is a cut away view of a sealable pouch containing a sensor connected to a circuit capable of exciting the sensor.
Figure 7:
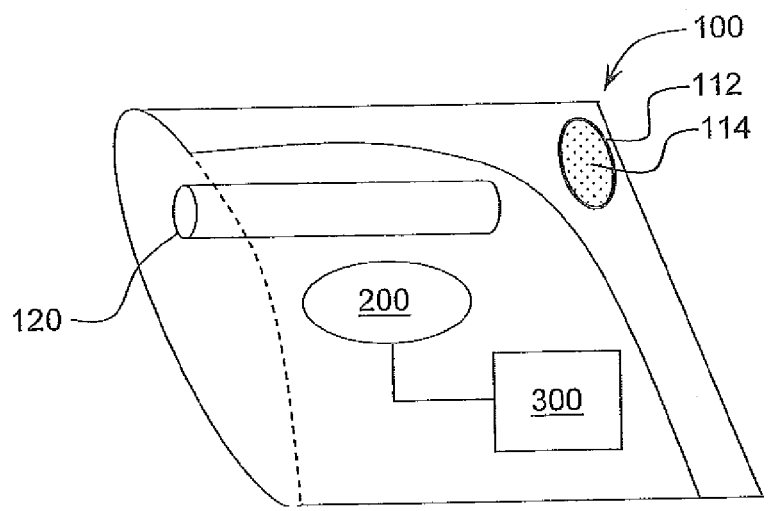
FIG. 7 is a cut away view of a sealable pouch containing a sensor connected to a circuit capable of exciting the sensor and a rupturable solution container.

To run-in the electrical aspects of a sensor contained in a sealable pouch 100, a sensor can be connected to a circuit designed to excite the sensor, such as, for example, the circuit shown in FIG. 1A. As shown in FIG. 6, a sensor 200 can be electrically connected to a circuit capable of exciting the sensor 300 with both the sensor 200 and circuit capable of electrically exciting the sensor 300 located within the sealable pouch 100. The circuit 300 can be provided in the sterilized sealable pouch 100 and can be activated within the sealable pouch 100 without exposing the sensor 200 to the outside environment. The circuit capable of electrically exciting the sensor 300 can be manually activated through the use of a force external to the sealable pouch 100 such as by the activation of a switch, remotely activated through the use of an external signal, or automatically activated upon the provision of a solution to the sealable pouch 100. For example, an electrical connection for activating the circuit 300 can be provided on a surface of the sealable pouch 100 and manually activated without opening the pouch or a complete circuit can be integrated into the sealable pouch 100 that is activated upon the provision of an electrolytic solution. As used herein, the phrase "excite the sensor" refers to providing an electrical signal to the sensor 200 such that the sensor achieves, remains at or close to, or approaches a condition at which it can take sensor readings with little or no additional electrical preparation. Such an electrical signal can include, for example, a current controlled constant or periodic potential provided by, for example, a current controlled voltage source that provides a constant voltage, which is applied to a reference electrode 12 and/or a working electrode 16 such as those shown in FIG. 3. The number and type of electrical signals can depend on the number and state the electrodes will need to be in when the sensor 300 is used for sensing. FIG. 7 shows an embodiment in which a circuit capable of electrically exciting the sensor 300 and alternatively a resealable portion 112 and/or a rupturable solution container 120 are included in a sealable pouch 100. In this embodiment, the circuit capable of electrically exciting the sensor 300 can be activated at or around the time the rupturable solution container 120 is ruptured through, for example, the use of a fluid sensor located within the pouch.

Methods for preparing a sensor for use include providing a solution such as an electrolytic solution to a sterilized packaging containing a sensor without compromising the sterilizable packaging then allowing the sensor to stabilize in the solution. The sensor can be connected to a sensor activating circuit before or after the provision of the electrolytic solution. If the sensor is connected to a sensor activating circuit after solution is provided, the sensor activating circuit can be activated and the electrical aspects of the system can be run-in. The circuit can be activated by an external force, such as moving a switch, or automatically when the solution is provided. For example, solution can be provided and a switch activated to initiate the sensor activating circuit. For further example, solution can be provided and the sensor activating circuit can be activated by the presence of solution. Such sensors are described above and can include a glucose sensor. Examples of solutions for use with the apparatus and methods herein include, but are not limited to, buffer solutions, saline solutions, solutions containing electrolytes or other chemicals needed either for chemical reactions at the electrodes or for other electrode preparations, and mixtures thereof.

The several sensor run-in preparations described herein may or may not completely prepare a sensor for use. However, the sensor will be closer to an operational state than if the run-in preparations did not occur. When a glucose sensor, for example, is in use, hydrogen peroxide is produced in the presence of glucose at the electrode, the hydrogen peroxide is converted to electrons, and the electrons are measured at the working electrode. When a glucose sensor is first exposed to glucose there is a lag time before electrons are produced at a steady-state indicating the glucose level. After a steady-state is obtained, if voltage is discontinued to the electrodes, the sensor depolarizes, i.e., electrons are no longer attracted to the working electrode, but the reaction to form hydrogen peroxide still occurs. Thus, when a potential is again applied to the electrodes the excess hydrogen peroxide needs to be converted and the measurement from the sensor will appear higher than the actual glucose level. In both the start up and restart scenarios, the sensor takes some time to equilibrate and provide a steady-state reading indicative of the glucose level.

Also provided herein, are apparatus for stabilizing a sensor that is being prepared for use, e.g., during initial implantation, or already in use. These apparatus include a circuit connectable to a sensor for providing a signal, such as an electrical current or potential, to the sensor. Such a signal can include, for example, a constant or periodic potential applied to a reference electrode 12 and/or a working electrode 16 such as those shown in FIG. 3. The signal chosen to be sent to the sensor is one that prevents the sensor from becoming destabilized prior to being connected or upon being disconnected from a monitoring device. For example, the circuit can prevent the sensor from becoming depolarized. When the electrodes of a sensor become depolarized the sensor cannot be used immediately and another run-in period becomes necessary to repolarize the electrodes. A glucose sensor, for example, has a chemical component to maintain a stabilized state, i.e., if a glucose sensor is in the presence of glucose, hydrogen peroxide conversion takes place and excess hydrogen peroxide will need to be converted prior to obtaining accurate glucose level readings. However, if the glucose sensor retains its electrical potential excess hydrogen peroxide does not accumulate at the working electrode.

Figure 8:
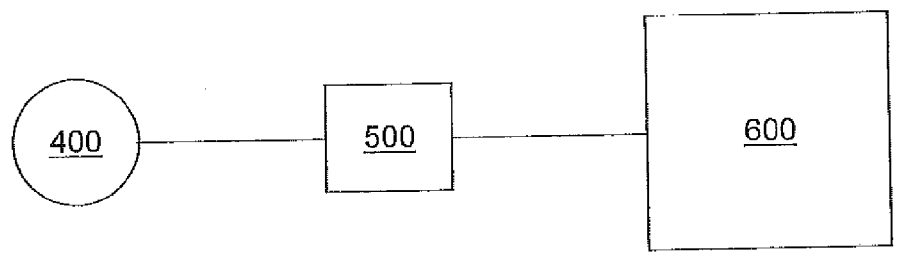
FIG. 8 is a block diagram showing a configuration of a sensor connected in series to a circuit then to a monitoring device.
Figure 9:
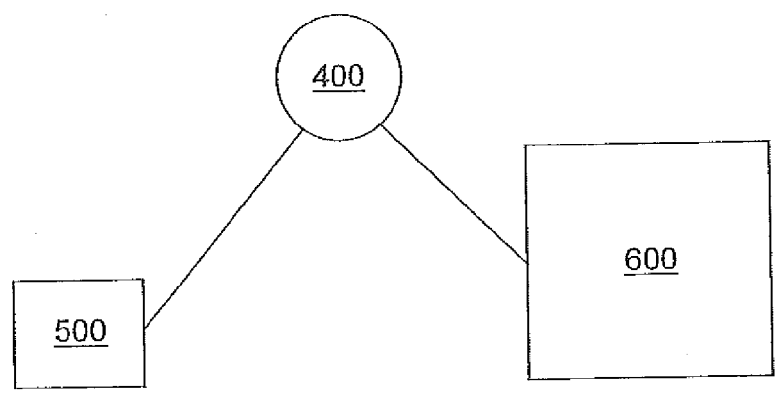
FIG. 9 is a block diagram showing an alternative configuration of the circuit connected to the sensor and monitoring device connected to the sensor not in series.

As shown in FIG. 8, a sensor 400 can be connected to a circuit 500 and a monitoring device 600. FIG. 9 shows an alternative configuration in which the circuit 500 and monitoring device 600 are not connected to the sensor 400 in series, i.e., there are two possible connections to the sensor 400. In either configuration, to stabilize a sensor 400, i.e., maintain the sensor 400 in an active, useable state, a signal is continually provided to excite the sensor 400. Maintaining a signal to excite the sensor 400 is accomplished by maintaining a connection with a power source, such as a power source from either the circuit 500 or monitoring device 600. Alternatively, a signal to excite the sensor 400 is provided by another source, such as a battery of a charged capacitor communicating with the sensor 400. As described above, the sensor 400 can be an electrochemical sensor such as a glucose sensor.

Figure 10:
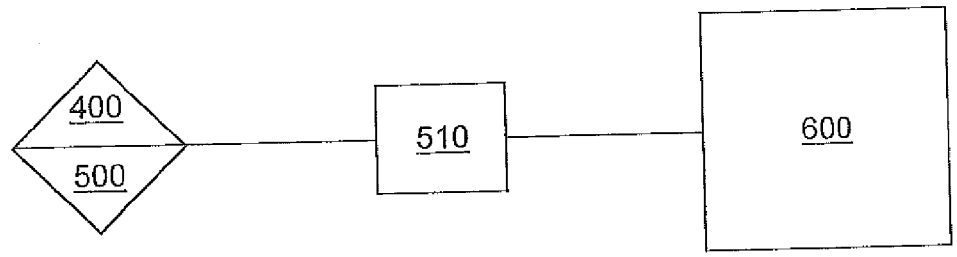
FIG. 10 is a block diagram showing an alternative configuration with the circuit and the sensor integrated into a single unit and connected to a patient monitoring cable and a monitoring device in series.

The circuit 500 can be configured to connect to a sensor 400 continuously such that the circuit 500 is connected to the sensor 400 both when the sensor 400 is connected to and when the sensor 400 is disconnected from a monitoring device 600. Alternatively, a circuit 500 can be configured to be capable of being removed from the sensor 400 when the sensor 400 is connected to a monitoring device 600 or an alternate signal source and reconnected to the sensor 400 when the sensor 400 is to be disconnected from the monitoring device 600, with the provision that a signal to excite the sensor 400 is continually applied to the sensor 400. In a further alternative as shown in FIG. 10, the sensor 400 and circuit 500 are integrated into a single unit. In an additional alternative, the sensor 400 and circuit 500 are integrated into a single unit that is disposable.

Figure 11:
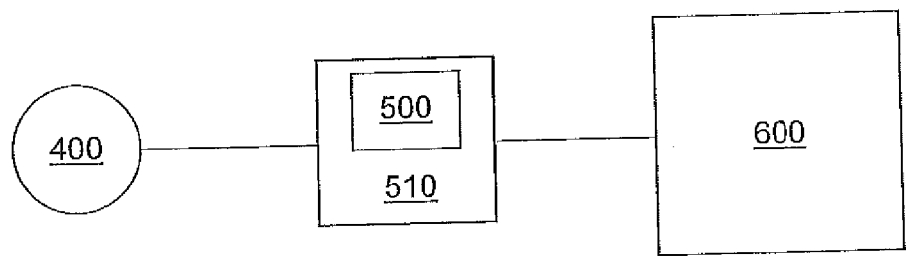
FIG. 11 is a block diagram showing an alternative configuration with the circuit integrated into a patient monitoring cable such that the circuit is not removed when the sensor is in use.
Figure 12:
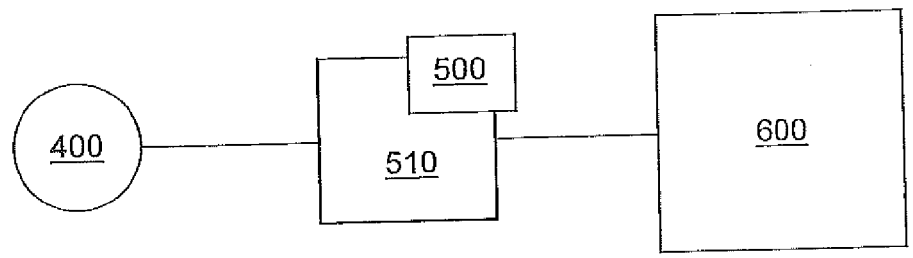
FIG. 12 is a block diagram showing an alternative configuration with the circuit removeably connectable to a patient monitoring cable.

If the sensor 400 is connected to, for example, a patient monitoring cable 510, the circuit 500 can either be integrated into the cable 510 so it is not removed when the sensor 400 is in use as shown in FIG. 11, or the circuit 500 can be removeably connectable to the patient monitoring cable 510 as shown in FIG. 12. If the circuit 500 is removeably connectable to a patient monitoring cable 510, the monitoring device 600 to which the patient monitoring cable 510 is connected is capable of providing a signal to the sensor 400. Then, when the patient monitoring cable 510 is to be disconnected from the monitoring device 600, the circuit 500 provides a signal to the sensor 400 in the absence of the signal from the monitoring device 600. When the circuit 500 is integrated into a device, such as a patient monitoring cable 510, and the circuit 500 is not disconnected from the sensor 400 when the sensor 400 is connected to a monitoring device 600, the circuit 500 can be configured such that there is a manual mechanism for disconnecting the circuit 500 from the sensor 400 or the circuit 500 can be configured to automatically disconnect in the presence of another signal source, e.g., a voltage source. Alternatively, when the sensor 400 is connected to the monitoring device 600, the circuit 500 can continue to provide a signal to the sensor 400 with the monitoring device 600 providing power for the circuit 500 to operate or charging the power source of the circuit 500. Such circuit aspects are easily designed and implemented by those of skill in the art.

Figure 13:
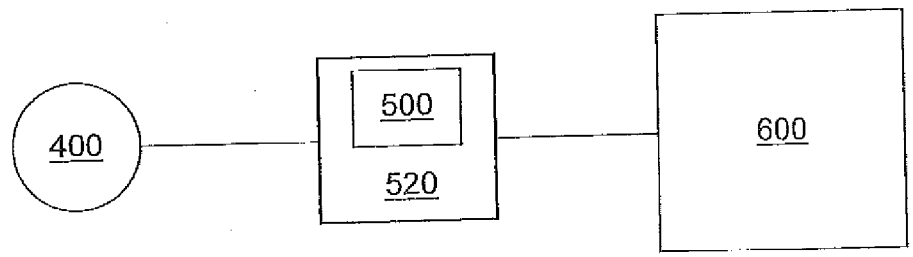
FIG. 13 is a block diagram showing an alternative configuration with the circuit housed in a module to which the sensor and monitoring device can be connected.

As shown in FIG. 13, circuits 500 such as those described can be housed in modules 520 to which a sensor 400 can be connected and which can be in turn connected in series to a monitoring device 600. A monitoring device 600 can be configured to accept a module 520 containing a circuit 500.

A circuit 500 can include a rechargeable voltage source, e.g., a rechargeable battery. The circuit 500 can be configured to recharge the rechargeable power source when the circuit is connected to a monitoring device. Alternately, the rechargeable power source can be charged or recharged at a charging station which can be used to initially charge a rechargeable voltage source connected to a circuit 500 or maintain a charge if a sensor 400 remains disconnected from a monitoring device 600 for an extended period of time. A recharging station can have multiple positions for simultaneously charging multiple circuits 500.

As an additional feature, a recordable storage medium (not shown) can be included in the circuit 500. The recordable storage medium, such as an electrically erasable programmable read-only memory (EEPROM), can, for example, record data corresponding to the sensor 400. Data corresponding to the sensor 400 can include time data, such as total time in service or time since last connected to a monitoring device 600, calibration data, or sensor reading or condition data. Such data can, for example, be recorded from sensor readings, internal timing devices, or other sensor 400 or circuit 500 generated data, or transferred to the circuit 500 prior to the sensor 400 being disconnected from a monitoring device 600. Then, conversely, when the sensor 400 is connected to a different monitoring device 600, some or all of the data can be transferred to the newly connected (or reconnected) monitoring device 600 to enable the new (or reconnected) monitoring device 600 to prepare the sensor 400 to begin collecting data, thereby reducing the needed run-in and/or calibration time. If a large enough memory capacity is available, all or many of the measurements made by a sensor 400 during a monitoring period could be stored in the circuit 500 for retrieval by a number of different monitors. Further features of the circuit 500 can include the ability to wirelessly transmit data to a monitoring device when a sensor 400 is detached from the monitoring device and the ability to log readings upon disconnect (either accidental or intentional) for transmittal to a monitoring device when reattached.

Circuits 500 such as those described can be housed in modules to which a sensor 400 can be connected and which can be in turn connected in series to a monitoring device 600. Such a circuit 500 can also be integrated into a device containing a sensor 400. A monitoring device 600 can be configured to accept a module containing a circuit 500. Further, sensors 400 can, for example, be incorporated into devices including medical devices such as patient monitoring cables. Circuits 500 can be, for example, incorporated into devices incorporating sensors or devices designed to connect to sensors. Where a storage capacitor is used as a signal source as described above, it can also be incorporated into devices in the same manner as the circuit 500.

The present invention is not limited in scope by the embodiments disclosed herein which are intended as illustrations of a few aspects of the invention and any embodiments which are functionally equivalent are within the scope of this invention. Various modifications of the apparatus and methods in addition to those shown and described herein will become apparent to those skilled in the art and are intended to fall within the scope of the appended claims. Further, while only certain representative combinations of the apparatus and method steps disclosed herein are specifically discussed in the embodiments above, other combinations of the apparatus components and method steps will become apparent to those skilled in the art and also are intended to fall within the scope of the appended claims. Thus a combination of components or steps may be explicitly mentioned herein; however, other combinations of components and steps are included, even though not explicitly stated. The term "comprising" and variations thereof as used herein is used synonymously with the term "including" and variations thereof and are open, non-limiting terms.

What is claimed is:

1. A method of preparing a sensor for use comprising:
   providing an electrolyte solution to a sterilized packaging containing
      an electrochemical glucose sensor connected to a sensor activating circuit without compromising the sterilized packaging, the electrochemical glucose sensor comprising a working electrode and a glucose oxidase containing reagent layer covered by a glucose selective membrane configured to react with glucose to provide hydrogen peroxide about the electrode;
   activating the sensor activating circuit; and
   allowing the electrochemical glucose sensor reagent layer to stabilize, with respect to polarization, in the electrolyte solution.

2. The method of claim 1, wherein the electrochemical glucose sensor is prevented from depolarizing.

3. The method of claim 1, wherein the electrolyte solution is provided via a resealable port in the sterilized packaging.

4. The method of claim 1, wherein the electrolyte solution is provided via a rupturable solution container.

5. The method of claim 1, wherein the circuit is activated when the electrolyte solution is provided.

6. The method of claim 1, further comprising the steps of:
   connecting or disconnecting the electrochemical glucose sensor to a monitoring device;
   wherein the circuit provides a signal to the electrochemical glucose sensor that prevents the electrochemical glucose sensor from becoming destabilized when connected or disconnected from the monitoring device.

7. The method of claim 6, wherein the signal is one of a continuous or a periodic electrical potential or a continuous or a periodic electrical current.

* * * * *